(12) United States Patent
Ichihashi et al.

(10) Patent No.: US 6,303,099 B1
(45) Date of Patent: Oct. 16, 2001

(54) PROCESS FOR PRODUCING PENTACYL-TYPE CRYSTALLINE ZEOLITES AND A PROCESS FOR PRODUCING ε-CAPROLACTAM USING THE SAME

(75) Inventors: Hiroshi Ichihashi, Otsu; Keisuke Sugita, Niihama; Makoto Yako, Takatsuki, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/605,473

(22) Filed: Jun. 28, 2000

(30) Foreign Application Priority Data

Jun. 30, 1999 (JP) .................................................. 11-185746
Jun. 30, 1999 (JP) .................................................. 11-185747

(51) Int. Cl.[7] .............................. C01B 39/36; B01J 29/40
(52) U.S. Cl. .................. 423/705; 423/707; 423/DIG. 22; 423/DIG. 29; 423/DIG. 34; 502/77; 502/86
(58) Field of Search ..................................... 423/705, 707, 423/DIG. 22, DIG. 29, DIG. 34; 502/77, 86

(56) References Cited

U.S. PATENT DOCUMENTS

| | | |
|---|---|---|
| 3,702,886 * | 11/1972 | Argauer . |
| 3,709,979 * | 1/1973 | Chu . |
| 4,385,042 * | 5/1983 | Whitehurst et al. . |
| 4,709,024 | 11/1987 | Sato et al. . |
| 4,968,793 | 11/1990 | Kitamura et al. . |
| 5,240,892 * | 8/1993 | Klocke . |
| 5,403,801 | 4/1995 | Kitamura et al. . |
| 5,624,658 * | 4/1997 | Fitoussi et al. ...................... 423/702 |

FOREIGN PATENT DOCUMENTS

| | | |
|---|---|---|
| 0021674A1 | 1/1981 | (EP) . |
| 021 675-A * | 1/1981 | (EP) . |
| 0026963A1 | 4/1981 | (EP) . |
| 0129239A2 | 12/1984 | (EP) . |
| 0380364A2 | 8/1990 | (EP) . |
| 1567948 | 5/1980 | (GB) . |
| WO-80/02026-A * | 10/1980 | (WO) . |

* cited by examiner

*Primary Examiner*—David R Sample
(74) *Attorney, Agent, or Firm*—Birch, Stewart, Kolasch & Birch, LLP

(57) ABSTRACT

A process for producing a pentacyl-type crystalline zeolite is provided which comprises the steps of (i) preparing a mixture of a silicon compound, water and tetrapropyl ammonium hydroxide, (ii) conducting a hydrothermal reaction of the mixture to obtain a reaction mixture containing zeolite crystals, (iii) separating zeolite crystals from the reaction mixture to collect a remaining solution, (iv) calcinating the resulting zeolite crystals, (v) treating the calcinated zeolite crystals with a solution such as ammonia water and (vi) recycling the solution collected in step (iii) to step (i), wherein in the mixture prepared in step (i) a molar ratio of hydroxide ion to silicon is from about 0.1 to about 0.4 and a molar ratio of potassium to silicon is about 0.1 or less. With this process, a zeolite catalyst having good performance can be produced with good reproducibility.

9 Claims, No Drawings

PROCESS FOR PRODUCING PENTACYL-TYPE CRYSTALLINE ZEOLITES AND A PROCESS FOR PRODUCING ε-CAPROLACTAM USING THE SAME

BACKGROUND OF THE INVENTION

1. Field of the Invention

The present invention relates to a process for producing pentacyl-type crystalline zeolites and a process for producing ε-caprolactam by use of the same.

2. Description of the Related Art

ε-Caprolactam is an important and fundamental chemical material used as a starting material for producing nylon etc., and one of proposed processes for producing ε-caprolactam is Beckmann rearrangement (gaseous-phase Beckmann rearrangement) of cyclohexanone oxime under gaseous-phase reaction conditions in the presence of a pentacyl-type crystalline zeolite catalyst (e.g., JP-A 2-275850 and JP-A 2-250866).

Pentacyl-type crystalline zeolites are produced by hydrothermal synthesis reaction of a silicon compound such as tetraalkyl orthosilicate by using a compound such as tetrapropyl ammonium hydroxide as the so-called template agent. Such a process has problems such that a pentacyl-type crystalline zeolite having high activity cannot always be obtained. Further, in such a process, the unreacted silicon compound and the unreacted tetrapropyl ammonium hydroxide remain in the residual solution obtained after the product zeolites were recovered, and thus their recycling for use is considered appropriate, but there is a problem in that even if such unreacted materials are recycled and used as the starting materials in the hydrothermal synthetic reaction, a pentacyl-type zeolite having high catalytic activity is hardly obtained with good reproducibility.

SUMMARY AND OBJECTS OF THE INVENTION

Under such circumstances, the present inventors made extensive study with the aim of finding a process wherein a pentacyl-type crystalline zeolite catalyst having high activity can be produced with good reproducibility, while the unreacted silicon compound and tetrapropyl ammonium hydroxide can be effectively utilized through recycling. As a result, the present inventors have found that the amounts of specific components contained in the starting materials are regulated in production of a pentacyl-type crystalline zeolite catalyst, whereby a zeolite catalyst having superior performance can be produced with good reproducibility while the unreacted starting materials can be effectively utilized through recycling, thus completing the present invention.

That is, the present invention provides a process for producing a pentacyl-type crystalline zeolite which comprises the steps of (i) preparing a mixture of a silicon compound, water and tetrapropyl ammonium hydroxide, (ii) conducting a hydrothermal reaction of the mixture to obtain a reaction mixture containing zeolite crystals, (iii) separating zeolite crystals from the reaction mixture to collect a remaining solution, (iv) calcinating the resulting zeolite crystals, (v) treating the calcinated zeolite crystals with an aqueous solution containing a compound selected from ammonia and ammonium salts to obtain a pentacyl-type crystalline zeolite and (vi) recycling the solution collected in step (iii) to the mixture-preparing step (i), wherein a molar-ratio composition of the mixture prepared in step (i) is adjusted so that a molar ratio of hydroxide ion to silicon falls within a range of from about 0.1 to about 0.4 and that a molar ratio of potassium to silicon is about 0.1 or less.

Further, the present invention provides a process for producing ε-caprolactam which comprises subjecting cyclohexanone oxime to a gaseous phase catalytic rearrangement reaction using a pentacyl-type crystalline zeolite obtained by the process described above.

DETAILED DESCRIPTION OF THE INVENTION

A pentacyl-type crystalline zeolite in the present invention is produced by:

(i) preparing a mixture of a silicon compound, water and tetrapropyl ammonium hydroxide,
(ii) conducting a hydrothermal reaction of the mixture to obtain a reaction mixture containing zeolite crystals,
(iii) separating zeolite crystals from the reaction mixture to collect a remaining solution,
(iv) calcinating the resulting zeolite crystals,
(v) treating the calcinated zeolite crystals with an aqueous solution containing a compound selected from ammonia and ammonium salts to obtain a pentacyl-type crystalline zeolite and
(vi) recycling the solution collected in step (iii) to the mixture-preparing step (i).

In the process, the mixture in step (i) is prepared so as to have such a molar-ratio composition that a molar ratio of hydroxide ion to silicon falls within a range of from about 0.1 to about 0.4 and that a molar ratio of potassium to silicon is about 0.1 or less. When a pentacyl-type crystalline zeolite catalyst is produced by the process of the present invention described above, a zeolite catalyst having superior performance can be produced with good reproducibility, while the unreacted starting materials can be used effectively through recycling thereof.

The silicon compound used in step (i) includes e.g. tetraalkyl orthosilicates. Examples of such tetraalkyl orthosilicates include tetramethyl orthosilicate, tetraethyl orthosilicate, tetrapropyl orthosilicate and tetrabutyl orthosilicate. One or more compounds selected from these orthosilicates are preferably used, among which tetraethyl orthosilicate is preferably used.

In the mixture prepared in the step (i), a molar ratio of each component to silicon is controlled as follows: a molar ratio of water to silicon is preferably about 5 to about 100, more preferably about 10 to about 60, a molar ratio of tetrapropyl ammonium hydroxide to silicon is preferably about 0.1 to about 0.3, more preferably 0.15 to about 0.3, a molar ratio of carbonate ion to silicon is preferably about 0.06 or less, more preferably about 0.04 or less (smaller ratio than that is much better), and a molar ratio of potassium is preferably about 0.1 or less, more preferably about 0.04 to about 0.1.

In the mixture prepared in the step (i), a molar ratio of hydroxide ion to silicon falls within a range of from about 0.1 to about 0.4. When a molar ratio of carbonate ion to silicon in the mixture falls within a range of from about 0.06 to about 0.12, it is preferred that the molar ratio of hydroxide ion to silicon falls within a range of from about 0.2 to about 0.4. When a molar ratio of carbonate ion to silicon in the mixture is about 0.06 or less, the molar ratio of hydroxide ion to silicon may fall within a range of from about 0.1 to about 0.3.

It is preferred that the mixture in step (i) is prepared using tetrapropyl ammonium hydroxide in an amount of from about 0.2 to about 1 molar time as large as the total amount of the anions therein (excluding hydroxide ion and bromide ion) which exceeds an amount equivalent to the molar ratio of about 0.03 of said anion to silicon, in addition to the amount used for conducting the hydrothermal reaction of said mixture.

In the composition of the mixture, when the molar ratio of tetrapropyl ammonium hydroxide to silicon is less than about 0.1, or the molar ratio of hydroxide ion to silicon is less than about 0.1, then the size of the resulting zeolite crystals is enlarged, and as a result, their total area of outer surface of the crystals is decreased so that zeolites obtained after calcination may not achieve sufficient conversion of starting material(s) in various reactions such as in production of $\epsilon$-caprolactam. On the other hand, when the molar ratio of tetrapropyl ammonium hydroxide to silicon is more than about 0.3, or the molar ratio of hydroxide ion to silicon is more than about 0.4, then the resulting zeolite crystals are small and not preferred since their filtration in step (iii) tends to be difficult. When the molar ratio of carbonate ion to silicon is more than about 0.06 and the molar ratio of hydroxide ion to silicon is less than about 0.2, or when the molar ratio of potassium to silicon is more than about 0.1, then the resulting zeolite may not achieve a sufficient conversion of cyclohexanone oxime in the production of $\epsilon$-caprolactam from cyclohexanone oxime, and the selectivity for $\epsilon$-caprolactam tends to be decreased.

Even if potassium is not contained in the mixture, it is potential to obtain a zeolite having superior catalytic performance to that of a zeolite obtained when the molar ratio of potassium to silicon is more than about 0.1. However, potassium is preferably contained in a small amount, specifically at a molar ratio of about 0.04 or more to silicon.

The molar ratio of hydroxide ion or potassium to silicon can be suitably adjusted by regulating the composition and amount of the silicon compound and tetrapropyl ammonium hydroxide used in step (i) or by using sodium hydroxide or potassium hydroxide in a controlled amount. Since carbonate ion may attribute to impurities contained in the starting materials (such as tetrapropyl ammonium hydroxide) of the mixture, it is appropriate that the content of such impurities (that is a possible source of carbonate ion) in the starting materials is controlled, and also that during storage, the starting materials are managed so as to minimize dissolution of carbon dioxide therein.

In the present invention, the content of each component in the mixture prepared in step (i) is measured as follows: the content of silicon was measured by an ICP emission method, the contents of tetrapropyl ammonium hydroxide, carbonate ion and bromide ion by ion chromatography, and the contents of potassium and sodium by an atomic absorption method. The content of hydroxide ion is measured as follows: The content of carbonate ion in the mixture previously measured by ion chromatography is subtracted from the total content of carbonate ion and hydroxide ion which is measured by a neutralizing titration method in which the mixture is completely neutralized with 0.2 N hydrochloric acid, to obtain the content of hydroxide ion. The water content can be determined by subtracting the respective measured contents of the components from the total amount of the mixture.

In step (i), nitrates and alkoxides such as isopropoxide, which are composed of an element selected from aluminum, gallium, boron, titanium and zinc, may be used if necessary. In the mixture prepared in step (i), an atomic ratio of silicate to the total of aluminum, gallium, boron, titanium and zinc is preferably about 500 or more, and more preferably about 1000 or more. When this atomic ratio is less than about 500, thermostability of the resulting zeolites and selectivity in a catalytic reaction tend to be lowered.

The atomic ratio can be suitably regulated by suitably controlling the composition of the silicon compound and tetrapropyl ammonium hydroxide used in step (i), and/or by using a compound containing an element selected from potassium, aluminum, gallium, boron, titanium and zinc in a controlled amount.

The mixture prepared in step (i) is used in hydrothermal synthesis in step (ii).

Hydrothermal synthesis is conducted under a temperature of from about 80° C. to about 160° C. for about 1 hour to about 200 hours.

From the reaction mixture obtained after the hydrothermal synthesis, zeolite crystals is then separated in step (iii) to collect a remaining solution. For this separation, filtration is preferably used.

The zeolite crystals separated in step (iii) are dried if necessary and then calcinated in step (iv). This calcination is conducted at a temperature in a range of from about 400 to about 600° C. in the air, in nitrogen or in a mixture gas of the air and nitrogen.

The zeolite crystals obtained in step (iv) are then treated in step (v) with an aqueous solution containing a compound selected from ammonia and ammonium salts. Such treatment can be carried out at a temperature of from about 50 to about 100° C. for about 0.1 to about 12 hours. When ammonia water or an aqueous mixture of ammonia and an ammonium salt is used, pH thereof is preferably regulated in the range of from about 9 to about 13. Examples of the ammonium salt used include ammonium nitrate, ammonium chloride and ammonium sulfate. In particular, ammonium nitrate is preferably used. By such treatment, the catalytic activity of the zeolite crystals obtained in step (iv) is further improved.

The zeolite crystals obtained after the treatment in step (v) may be calcinated again after drying.

The solution obtained in step (iii) may be recycled as a part of the mixture used in step (i).

In recycling the solution to step (i), it is appropriate that the solution is managed so as to minimize dissolution of carbon dioxide therein during storage etc. Specifically, it is appropriate that the solution is stored in an atmosphere such as nitrogen gas or carbon dioxide-free air in a sealed vessel.

When an alcohol is produced as byproduct by hydrothermal synthesis reaction in step (ii), for example, when ethanol is produced as byproduct by use of tetraethyl orthosilicate as the silicon compound, a part or the whole of the alcohol is preferably removed by a technique such as distillation from the solution obtained by the separation of hydrothermal synthesis reaction mixture, before the solution is recycled for use.

Using a pentacyl-type crystalline zeolites thus obtained, $\epsilon$-caprolactam can be efficiently produced by the gaseous phase catalytic reaction of cyclohexanone oxime.

Such gaseous phase catalytic reaction can be effected in either a fixed-bed system or a fluidized-bed system. A reaction temperature is preferably about 250 to about 500° C., more preferably about 300 to about 450° C., and most preferably about 300 to about 400° C.

A reaction pressure is not particularly limited and may be usually about 10 kPa to about 0.5 MPa. A feed rate of the starting material cyclohexanone oxime per kilogram of the pentacyl-type crystalline zeolite catalyst, that is, the space velocity WHSV of the starting material cyclohexanone oxime may be usually about 0.1 to about 40 $hr^{-1}$, preferably about 0.2 to about 20 $hr^{-1}$, and more preferably about 0.5 to about 10 $hr^{-1}$.

Separation and purification of $\epsilon$-caprolactam from the reaction mixture obtained after the gaseous phase catalytic reaction can be conducted in a known method. For example, the reaction gas obtained as the reaction mixture is condensed by cooling, then extracted, distilled or crystallized, whereby purified ε-caprolactam can be obtained.

EXAMPLES

The present invention is described in more detail by following Examples, which should not be construed as a limitation upon the scope of the present invention.

The space velocity WHSV, the degree of conversion of cyclohexanone oxime, and the selectivity for ε-caprolactam were calculated respectively in the following formulae:

$$WHSV\ (hr^{-1})=O/C$$

Conversion of cyclohexanone oxime (%)=[(X−Y)/X]×100
Selectivity for ε-caprolactam (%)=[Z/(X−Y)]×100

The meanings of O, C, X, Y and Z are as follows:

O=Feed rate of cyclohexanone oxime (kg/hr)
C=Amount by weight of catalyst (kg)
X=Molar amount of fed cyclohexanone oxime
Y=Molar amount of unreacted cyclohexanone oxime
Z=Molar amount of formed ε-caprolactam

Example 1

In a 1.5-L stainless steel autoclave, 208 g of tetraethyl orthosilicate (Si(OC$_2$H$_5$)$_4$), 114 g of 41% aqueous tetra-n-propyl ammonium hydroxide solution (carbonate ion content: 630 ppm) and 581 g of water were placed and stirred vigorously for 120 minutes. The molar ratios of water, tetra-n-propyl ammonium cation, hydroxide ion and carbonate ion to silicon in the resulting reaction mixture were 36, 0.23, 0.23 and 0.0012, respectively. While the temperature in the autoclave was kept at 105° C., the mixture was subjected to hydrothermal synthesis for 96 hours under stirring at a velocity of 300 rpm or more. The resulting reaction mixture was filtered off and washed continuously with de-ionized water until the pH of the filtrate reached about 8, to obtain white crystals. The resulting crystals were dried at 110° C. for 16 hours, calcinated at 530° C. for 1 hour in a nitrogen stream, and then calcinated at 530° C. for 1 hour in an air stream, to obtain powdery white crystals. As a result of analysis of powdery X-ray diffraction of the crystals, the crystals were identified as pentacyl-type zeolite.

Into an autoclave, 10 g of the obtained powdery white crystals and 278 g of the mixture of aqueous ammonium nitrate solution (7.5% by weight, 110 g) and ammonia water (25% by weight, 168 g) were placed, and kept at 90° C. for 1 hour under stirring. From the resulting mixture, the crystals were separated by filtration. After such treatment (with the mixture of aqueous ammonium nitrate solution and ammonia water) and filtration were conducted repeatedly three times in total, the resulting crystals were washed with water and dried. The catalyst thus obtained is referred to hereinafter as catalyst A-1.

The catalyst A-1 was sieved through a 24 to 48 mesh, and 0.375 g of the sieved catalyst was packed into a quartz glass reaction tube with an internal diameter of 1 cm to form a catalyst layer which was then preliminarily heat-treated at 350° C. for 1 hour while passing nitrogen therethrough (4.2 L/hr). Then, after the temperature of the catalyst layer was decreased to 325° C., a mixed solution consisting of cyclohexanone oxime/methanol at a ratio of 1/1.8 was fed to the reaction tube at a feed rate of 8.4 g/hr, whereby the cyclohexanone oxime was reacted. The space velocity WHSV was 8 hr.$^{-1}$. The reaction was continued for 5.5 hours. From 0.5 to 5.5 hours after the reaction was initiated, the reaction mixture gas was captured and analyzed by gas chromatography. As a result, the conversion of cyclohexanone oxime was 99.5%, and the selectivity for ε-caprolactam was 96.2%.

Example 2

In a 1.5-L stainless steel autoclave 125 g of tetraethyl orthosilicate (Si(OC$_2$H$_5$)$_4$), 71.2 g of 40.3% aqueous tetra-n-propyl ammonium hydroxide solution (carbonate ion content: 3990 ppm), 0.371 g of potassium hydroxide and 349 g of water were placed and stirred vigorously for 120 minutes. The molar ratios of water, tetra-n-propyl ammonium cation, hydroxide ion and carbonate ion to silicon in the resulting reaction mixture were 36, 0.23, 0.24 and 0.0079, respectively. While the temperature in the autoclave was kept at 105° C., the mixture was subjected to hydrothermal synthesis for 96 hours under stirring at a velocity of 300 rpm or more. The resulting reaction mixture was filtered off and washed continuously with de-ionized water until the pH of the filtrate reached about 8, to obtain white crystals. The resulting crystals were dried at 110° C. for 16 hours, calcinated at 530° C. for 1 hour in a nitrogen stream, and then calcinated at 530° C. for 1 hour in an air stream, to obtain powdery white crystals. As a result of analysis of powdery X-ray diffraction of the crystals, the crystals were identified as pentacyl-type zeolite.

In an autoclave, 10 g of the obtained powdery white crystals was treated three times with a mixture of aqueous ammonium nitrate solution and ammonia water in the same manner as in Example 1, to obtain catalyst B-1.

ε-Caprolactam was produced in the same manner as in Example 1 except that the catalyst B-1 was used in place of the catalyst A-1 in the production of ε-caprolactam in Example 1. The conversion of cyclohexanone oxime was 98.4% and the selectivity for ε-caprolactam was 96.7%.

Example 3

In a 1.5-L stainless steel autoclave, 139 g of tetraethyl orthosilicate (Si(OC$_2$H$_5$)$_4$), 77.9 g of 40.5% aqueous tetra-n-propyl ammonium hydroxide solution (carbonate ion content, 9130 ppm; ammonium ion content, 5110 ppm) and 386 g of water were placed and stirred vigorously for 120 minutes. The molar ratios of water, tetra-n-propyl ammonium cation, hydroxide ion and carbonate ion to silicon in the resulting reaction mixture were 36, 0.23, 0.23 and 0.018, respectively. While the temperature in the autoclave was kept at 105° C., the mixture was subjected to hydrothermal synthesis for 96 hours under stirring at a velocity of 300 rpm or more. The resulting reaction mixture was filtered off and washed continuously with de-ionized water until the pH of the filtrate reached about 8, to obtain white crystals. The resulting crystals were dried at 110° C. for 16 hours, calcinated at 530° C. for 1 hour in a nitrogen stream, and then calcinated at 530° C. for 1 hour in an air stream, to obtain powdery white crystals. As a result of analysis of powdery X-ray diffraction of the crystals, the crystals were identified as pentacyl-type zeolite.

In an autoclave 10 g of the obtained powdery white crystals was treated three times with a mixture of aqueous ammonium nitrate solution and ammonia water in the same manner as in Example 1, to obtain catalyst C-1.

ε-Caprolactam was produced in the same manner as in Example 1 except that the catalyst C-1 was used in place of the catalyst A-1 in the production of ε-caprolactam in Example 1. The conversion of cyclohexanone oxime was 98.1% and the selectivity for ε-caprolactam was 96.3%.

Example 4

In a 1.5-L stainless steel autoclave, 115 g of tetraethyl orthosilicate ($Si(OC_2H_5)_4$), 65.8 g of 40.1% aqueous tetra-n-propyl ammonium hydroxide solution (carbonate ion content: 1.43%), 0.341 of g potassium hydroxide and 321 g of water were placed and stirred vigorously for 120 minutes. The molar ratios of water, tetra-n-propyl ammonium cation, hydroxide ion and carbonate ion to silicon in the resulting reaction mixture were 36, 0.23, 0.24 and 0.028, respectively. While the temperature in the autoclave was kept at 105° C., the mixture was subjected to hydrothermal synthesis for 96 hours under stirring at a velocity of 300 rpm or more. The resulting reaction mixture was filtered off and washed continuously with distilled water until the pH of the filtrate reached about 8, to obtain crystals. The resulting crystals were dried at 110° C. for 16 hours, calcinated at 530° C. for 1 hour in a nitrogen stream, and then calcinated at 530° C. for 1 hour in an air stream, to obtain powdery white crystals. As a result of analysis of powdery X-ray diffraction of the crystals, the crystals were identified as pentacyl-type zeolite.

In an autoclave, 10 g of the obtained powdery white crystals was treated three times with a mixture of aqueous ammonium nitrate solution and ammonia water in the same manner as in Example 1, to obtain catalyst D-1.

$\epsilon$-Caprolactam was produced in the same manner as in Example 1 except that the catalyst D-1 was used in place of the catalyst A-1 in the production of $\epsilon$-caprolactam in Example 1. The conversion of cyclohexanone oxime was 96.9% and the selectivity for $\epsilon$-caprolactam was 96.5%.

Example 5

In a 1.5-L stainless steel autoclave, 115 g of tetraethyl orthosilicate ($Si(OC_2H_5)_4$), 21.3% aqueous tetra-n-propyl ammonium hydroxide solution (carbonate ion content: 8247 ppm), 9 g of tetra-n-propyl ammonium bromide, 1.05 g of potassium hydroxide and 255 g of water were placed and stirred vigorously for 120 minutes. The molar ratios of water, tetra-n-propyl ammonium cation, hydroxide ion and carbonate ion to silicon in the resulting reaction mixture were 36, 0.32, 0.29 and 0.034, respectively. While the temperature in the autoclave was kept at 105° C., the mixture was subjected to hydrothermal synthesis for 48 hours under stirring at a velocity of 300 rpm or more. The resulting reaction mixture was filtered off and washed continuously with distilled water until the pH of the filtrate reached about 8, to obtain crystals. The resulting crystals were dried at 110° C. for 16 hours, calcinated at 530° C. for 3 hours in a nitrogen stream, and then calcinated at 530° C. for 3 hours in an air stream, to obtain powdery white crystals. As a result of analysis of powdery X-ray diffraction of the crystals, the crystals were identified as pentacyl-type zeolite.

In an autoclave, 10 g of the obtained powdery white crystals was treated three times with a mixture of aqueous ammonium nitrate solution and ammonia water in the same manner as in Example 1, to obtain catalyst E-1.

$\epsilon$-Caprolactam was produced in the same manner as in Example 1 except that the catalyst E-1 was used in place of the catalyst A-1 in the production of $\epsilon$-caprolactam in Example 1. The conversion of cyclohexanone oxime was 99.7% and the selectivity for $\epsilon$-caprolactam was 96.3%.

Example 6

In a 1.5-L stainless steel autoclave, 115 g of tetraethyl orthosilicate ($Si(OC_2H_5)_4$), 316 g of 12.4% aqueous tetra-n-propyl ammonium hydroxide solution (carbonate ion content: 1.22%) and 87 g of water were placed and stirred vigorously for 120 minutes. The molar ratios of water, tetra-n-propyl ammonium cation, hydroxide ion and carbonate ion to silicon in the resulting reaction mixture were 36, 0.35, 0.35 and 0.12, respectively. While the temperature in the autoclave was kept at 105° C., the mixture was subjected to hydrothermal synthesis for 48 hours under stirring at a velocity of 300 rpm or more. The resulting reaction mixture was filtered off and washed continuously with de-ionized water until the pH of the filtrate reached about 8, to obtain white crystals. The resulting crystals were dried at 110° C. for 16 hours, calcinated at 530° C. for 3 hours in a nitrogen stream, and then calcinated at 530° C. for 3 hours in an air stream, to obtain powdery white crystals. As a result of analysis of powdery X-ray diffraction of the crystals, the crystals were identified as pentacyl-type zeolite.

In an autoclave, 10 g of the obtained powdery white crystals was treated three times with a mixture of aqueous ammonium nitrate solution and ammonia water in the same manner as in Example 1, to tain catalyst F-1.

$\epsilon$-Caprolactam was produced in the same manner as in Example 1 except that the catalyst F-1 was used in place of the catalyst A-1 in the production of $\epsilon$-caprolactam in Example 1. The conversion of cyclohexanone oxime was 98.5% and the selectivity for $\epsilon$-caprolactam as 96.9%.

Comparative Example 1

In a 1.5-L stainless steel autoclave, 139 g of tetraethyl orthosilicate ($Si(OC_2H_5)_4$), 77.9 g of 40.5% aqueous tetra-n-propyl ammonium hydroxide solution (carbonate ion content, 5.18%; ammonium ion, 3.08%) and 386 g of water were placed and stirred vigorously for 120 minutes. The molar ratios of water, tetra-n-propyl ammonium cation, hydroxide ion and carbonate ion to silicon in the resulting reaction mixture were 36, 0.23, 0.23 and 0.10, respectively. While the temperature in the autoclave was kept at 105° C., the mixture was subjected to hydrothermal synthesis for 96 hours under stirring at a velocity of 300 rpm or more. The resulting reaction mixture was filtered off and washed continuously with distilled water until the pH of the filtrate reached about 8, to obtain white crystals. The resulting crystals were dried at 110° C. for 16 hours, calcinated at 530° C. for 1 hour in a nitrogen stream, and then calcinated at 530° C. for 1 hour in an air stream, to obtain powdery white crystals. As a result of analysis of powdery X-ray diffraction of the crystals, the crystals were identified as pentacyl-type zeolite.

In an autoclave, 10 g of the obtained powdery white crystals was treated three times with a mixture of aqueous ammonium nitrate solution and ammonia water in the same manner as in Example 1, to obtain catalyst G.

$\epsilon$-Caprolactam was produced in the same manner as in Example 1 except that the catalyst G was used in place of the catalyst A-1 in the production of $\epsilon$-caprolactam in Example 1. The conversion of cyclohexanone oxime was 32.4% and the selectivity for $\epsilon$-caprolactam was 93.4%.

Example 7

In a 1.5-L stainless steel autoclave, 208 g of tetraethyl orthosilicate ($Si(OC_2H_5)_4$), 468 g of 10% aqueous tetra-n-propyl ammonium hydroxide solution (potassium content: 0% by weight) and 227 g of water were placed and stirred vigorously for 120 minutes. While the temperature in the autoclave was kept at 105° C., the mixture was subjected to hydrothermal synthesis for 96 hours under stirring at a velocity of 300 rpm or more. The resulting reaction mixture was filtered off and washed continuously with distilled water until the pH of the filtrate reached about 8, to obtain white crystals. The resulting crystals were dried at 110° C. for 16 hours, calcinated at 530° C. for 3 hours in a nitrogen stream, and then calcinated at 530° C. for 3 hours in an air stream, to obtain powdery white crystals. As a result of analysis of powdery X-ray diffraction of the crystals, the crystals were identified as pentacyl-type zeolite.

In an autoclave, 12 g of the obtained powdery white crystals were placed, and 335 g of mixture of aqueous ammonium nitrate solution (7.5% by weight, 135 g) and ammonia water (28% by weight, 200 g) were placed, and kept at 90° C. for 1 hour under stirring. From the resulting mixture, the crystals were separated by filtration. After such treatment (with the mixture of aqueous ammonium nitrate solution and ammonia water) and filtration were conducted repeatedly three times in total, the resulting crystals were washed with water and dried. The catalyst thus obtained is referred to hereinafter as catalyst A-2.

$\epsilon$-Caprolactam was produced in the same manner as in Example 1 except that the catalyst A-2 was used in place of the catalyst A-1 in the production of $\epsilon$-caprolactam in Example 1. The conversion of cyclohexanone oxime was 99.8% and the selectivity for $\epsilon$-caprolactam was 96.1%.

Example 8

In a 1.5-L stainless steel autoclave, 208 g of tetraethyl orthosilicate ($Si(OC_2H_5)_4$), 114 g of 41% aqueous tetra-n-propyl ammonium hydroxide solution (potassium content: 1.1% by weight) and 581 g of water were placed and stirred vigorously for 120 minutes. The molar ratio of potassium to silicon in the resulting reaction mixture was 0.032. While the temperature in the autoclave was kept at 105° C., the mixture was subjected to hydrothermal synthesis for 96 hours under stirring at a velocity of 300 rpm or more. The resulting reaction mixture was filtered off and washed continuously with distilled water until the pH of the filtrate reached about 8, to obtain white crystals. The resulting crystals were dried at 110° C. for 16 hours, calcinated at 530° C. for 3 hours in a nitrogen stream, and then calcinated at 530° C. for 3 hours in an air stream, to obtain powdery white crystals. As a result of analysis of powdery X-ray diffraction of the crystals, the crystals were identified as pentacyl-type zeolite. The potassium content was 0.84% by weight based on the crystals (molar ratio of potassium to silicon: 0.013).

Into an autoclave, 12 g of the obtained powdery white crystals was treated three times with a mixture of aqueous ammonium nitrate solution and ammonia water in the same manner as in Example 1, to obtain catalyst B-2.

$\epsilon$-Caprolactam was produced in the same manner as in Example 1 except that the catalyst B-2 was used in place of the catalyst A-1 in the production of $\epsilon$-caprolactam in Example 1. The conversion of cyclohexanone oxime was 99.5% and the selectivity for $\epsilon$-caprolactam was 96.2%.

Example 9

In a 1.5-L stainless steel autoclave, 208 g of tetraethyl orthosilicate ($Si(OC_2H_5)_4$), 114 g of 41% aqueous tetra-n-propyl ammonium hydroxide solution (potassium content: 1.1% by weight), 0.87 g of 85% potassium hydroxide (commercially available reagent) and 581 g of water were placed and stirred vigorously for 120 minutes. The molar ratio of potassium to silicon in the resulting reaction mixture was 0.045. While the temperature in the autoclave was kept at 105° C., the mixture was subjected to hydrothermal synthesis for 96 hours under stirring at a velocity of 300 rpm or more. The resulting reaction mixture was filtered off and washed continuously with distilled water until the pH of the filtrate reached about 8, to obtain white crystals. The resulting crystals were dried at 110° C. for 16 hours, calcinated at 530° C. for 3 hours in a nitrogen stream, and then calcinated at 530° C. for 3 hours in an air stream, to obtain powdery white crystals. As a result of analysis of powdery X-ray diffraction of the crystals, the crystals were identified as pentacyl-type zeolite. The potassium content was 1.5% by weight based on the crystals (molar ratio of potassium to silicon: 0.023).

Into an autoclave, 12 g of the obtained powdery white crystals was treated three times with a mixture of aqueous ammonium nitrate solution and ammonia water in the same manner as in Example 1, to obtain catalyst C-2.

$\epsilon$-Caprolactam was produced in the same manner as in Example 1 except that the catalyst C-2 was used in place of the catalyst A-1 in the production of $\epsilon$-caprolactam in Example 1. The conversion of cyclohexanone oxime was 99.8% and the selectivity for $\epsilon$-caprolactam was 96.9%.

Example 10

In a 1.5-L stainless steel autoclave, 208 g of tetraethyl orthosilicate ($Si(OC_2H_5)_4$), 69 g of 41% aqueous tetra-n-propyl ammonium hydroxide solution (potassium content: 1.1% by weight), 3.7 g of 85% potassium hydroxide (commercially available reagent) and 290 g of water were placed and stirred vigorously for 120 minutes. The molar ratio of potassium to silicon in the resulting reaction mixture was 0.088. While the temperature in the autoclave was kept at 105° C., the mixture was subjected to hydrothermal synthesis for 96 hours under stirring at a velocity of 300 rpm or more. The resulting reaction mixture was filtered off and washed continuously with distilled water until the pH of the filtrate reached about 8, to obtain white crystals. The resulting crystals were dried at 110° C. for 16 hours, calcinated at 530° C. for 3 hours in a nitrogen stream, and then calcinated at 530° C. for 3 hours in an air stream to obtain powdery white crystals. As a result of analysis of powdery X-ray diffraction of the crystals, the crystals were identified as pentacyl-type zeolite. The potassium content was 3.4% by weight based on the crystals (molar ratio of potassium to silicon: 0.054).

In an autoclave, 12 g of the obtained powdery white crystals was treated three times with a mixture of aqueous ammonium nitrate solution and ammonia water in the same manner as in Example 1, to obtain catalyst D-2.

$\epsilon$-Caprolactam was produced in the same manner as in Example 1 except that the catalyst D-2 was used in place of the catalyst A-1 in the production of $\epsilon$-caprolactam in Example 1. The conversion of cyclohexanone oxime was 98.8% and the selectivity for $\epsilon$-caprolactam was 96.8%.

Comparative Example 2

In a 1.5-L stainless steel autoclave, 208 g of tetraethyl orthosilicate ($Si(OC_2H_5)_4$), 45 g of 41% aqueous tetra-n-propyl ammonium hydroxide solution (potassium content: 1.1% by weight), 7.5 g of 85% potassium hydroxide (commercially available reagent) and 290 g of water were placed and stirred vigorously for 120 minutes. The molar ratio of potassium to silicon in the resulting reaction mixture was 0.15. While the temperature in the autoclave was kept at 105° C., the mixture was subjected to hydrothermal synthesis for 96 hours under stirring at a velocity of 300 rpm or more. The resulting reaction mixture was filtered off and washed continuously with distilled water until the pH of the filtrate reached about 8, to obtain white crystals. The resulting crystals were dried at 110° C. for 16 hours, calcinated at 530° C. for 3 hours in a nitrogen stream, and then calcinated at 530° C. for 3 hours in an air stream to obtain powdery white crystals. As a result of analysis of powdery X-ray diffraction of the crystals, the crystals were identified as pentacyl-type zeolite. The potassium content was 8.2% by weight based on the crystals (molar ratio of potassium to silicon: 0.14).

In an autoclave, 12 g of the obtained powdery white crystals was treated three times with a mixture of aqueous ammonium nitrate solution and ammonia water in the same manner as in Example 1, to obtain catalyst H.

ε-Caprolactam was produced in the same manner as in Example 1 except that the catalyst H was used in place of the catalyst A-1 in the production of ε-caprolactam in Example 1. The conversion of cyclohexanone oxime was 80.5% and the selectivity for ε-caprolactam was 96.8%.

Comparative Example 3

In a 1.5-L stainless steel autoclave, 139 g of tetraethyl orthosilicate ($Si(OC_2H_5)_4$), 77.9 g of 41% aqueous tetra-n-propyl ammonium hydroxide solution (potassium content: 1.1% by weight), 11.2 g of 85% potassium hydroxide (commercially available reagent) and 386 g of water were placed and stirred vigorously for 120 minutes. The molar ratio of potassium to silicon in the resulting reaction mixture was 0.29. While the temperature in the autoclave was kept at 105° C., the mixture was subjected to hydrothermal synthesis for 96 hours under stirring at a velocity of 300 rpm or more, but no crystal could be obtained.

What is claimed is:

1. A process for producing a pentacyl-type crystalline zeolite, comprising the steps of:
   (i) preparing a mixture of a silicon compound, water and tetrapropyl ammonium hydroxide,
   (ii) conducting a hydrothermal reaction of the mixture to obtain a reaction mixture containing zeolite crystals,
   (iii) separating the zeolite crystals from the reaction mixture to collect a remaining solution,
   (iv) calcining the resulting zeolite crystals,
   (v) treating the calcined zeolite crystals with an aqueous solution containing a compound selected from the group consisting of ammonia and ammonium salts to obtain a pentacyl-type crystalline zeolite, and
   (vi) recycling the solution collected in step (iii) to the mixture preparing step (i), wherein a molar-ratio composition of the mixture prepared in step (i) is adjusted so that the molar ratio of the hydroxide ion to silicon falls within a range of from about 0.1 to about 0.4; that a molar ratio of potassium to silicon is about 0.1 or less; and that an atomic ratio of silicon to the total of aluminum, gallium, boron, titanium and zinc is about 500 or more.

2. The process according to claim 1, wherein the molar-ratio composition of the mixture prepared in step (i) is adjusted so that a molar ratio of carbonate ion to silicon is about 0.06 or less.

3. The process according to claim 2, wherein the molar-ratio composition of the mixture prepared in step (i) is adjusted so that a molar ratio of hydroxide ion to silicon falls within a range of from about 0.1 to about 0.3.

4. The process according to claim 1, wherein the molar-ratio composition of the mixture prepared in step (i) is adjusted so that a molar ratio of carbonate ion to silicon is about 0.12 or less and that a molar ratio of hydroxide ion to silicon falls within a range of from about 0.2 to about 0.4.

5. The process according to claim 1, 2 or 4, wherein the mixture in step (i) is prepared using at least one compound selected from the group consisting of sodium hydroxide and potassium hydroxide.

6. The process according to claim 1, 2 or 4, wherein the molar-ratio composition of the mixture prepared in step (i) is adjusted so that a molar ratio of potassium to silicon falls within a range of from about 0.04 to about 0.1.

7. The process according to claim 1, 2 or 4, wherein the mixture in step (i) is prepared using a compound containing an element selected from the group consisting of aluminum, gallium, boron, titanium and zinc.

8. The process according to claim 1, 2 or 4, wherein the silicon compound is a tetraalkyl orthosilicate and in step (vi) the solution collected in step (iii) is recycled to step (i) after removing a part or whole of alcohol, which is produced from the tetraalkyl orthosilicate.

9. The process according to claim 1, 2 or 4, wherein a molar-ratio composition of the mixture prepared in step (i) is adjusted so that molar ratios of water, tetrapropyl ammonium hydroxide and hydroxide ion to silicon are 5 to 100, 0.1 to 0.3 and 0.1 to 0.4, respectively.

* * * * *